(12) United States Patent
Aranyi et al.

(10) Patent No.: US 7,365,089 B2
(45) Date of Patent: Apr. 29, 2008

(54) TRIAZOLO-QUINOLIN DERIVATIVES USEFUL AS ADENOSINE RECEPTOR LIGANDS

(75) Inventors: Peter Aranyi, Budapest (HU); Laszlo Balazs, God (HU); Sandor Batori, Budapest (HU); Judit Bence, Budapest (HU); Kinga Boer, Pomáz (HU); Felix Hajdu, Budapest (HU); Zoltan Kapui, Budapest (HU); Endre Mikus, Budapest (HU); Tibor Szabo, Budapest (HU); Lajos T. Nagy, Mezotur (HU); Geza Timari, Vecses (HU); Katalin Urban-Szabo, Budapest (HU); Erzsebet Walcz, Budapest (HU)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 10/499,250

(22) PCT Filed: Dec. 17, 2002

(86) PCT No.: PCT/HU02/00143

§ 371 (c)(1),
(2), (4) Date: Jan. 13, 2005

(87) PCT Pub. No.: WO03/003968

PCT Pub. Date: Jul. 3, 2003

(65) Prior Publication Data

US 2005/0124648 A1      Jun. 9, 2005

(30) Foreign Application Priority Data

Dec. 21, 2001  (HU) .................................. P0105407

(51) Int. Cl.
*A61K 31/4196*   (2006.01)
*A61K 31/4406*   (2006.01)
*C07D 251/72*    (2006.01)

(52) U.S. Cl. ...................... 514/383; 514/338; 514/444; 514/461; 546/272.4; 548/258; 549/59; 549/472; 549/474

(58) Field of Classification Search .................. 546/82; 514/293, 383; 548/262.4, 269.4
See application file for complete search history.

(56) References Cited

U.S. PATENT DOCUMENTS 4,024,149 A * 5/1977 Winters et al. .............. 514/292
5,101,028 A   3/1992 Schefczik et al.

FOREIGN PATENT DOCUMENTS

DE       280109       6/1990
DE       280110       6/1990

OTHER PUBLICATIONS

Brown, R., et al., N-Alkylation and Electrophilic Substitution Reactions of 2-Methylpyrazolo [1,5-a] pyridin-5-ol and Related Compounds, Chemical Abstract No. 121:134019 (1994).
Brown, R. et al., The Pyrolytic Rearrangement of 1-Alkynoyl-3-Methylpyrazoles: Synthesis, Chemical Abstract No. 121:108613 (1994).
Hubler, D, et al., Prodn. of Triazolopyridine-Carbo-Nitrile Derivs, Useful as Cardiovascular Agents with Positive Inotropic Activity, Derwent Patent Abstract No. 199047 (2004).
Potts, K., et al., 1,2,4-Triazoles. XIII. Derivatives of the s-Triazolo 1,5-ajpyridine Ring System, J. Org. Chem., vol. 31, No. 3, pp. 260-265 (1996).
Selby, T. et al., 7-Phenyl-1,2,4-triazolo [1,5-a] Pyrimidines and Related Heterocycles. A New Family of Bleaching Herbicides., Chemical Abstract No. 118:2390 (1992).

* cited by examiner

*Primary Examiner*—Rebecca Anderson
*Assistant Examiner*—Yong Chu
(74) *Attorney, Agent, or Firm*—Jiang Lin; Michael D. Alexander

(57) ABSTRACT

The present invention relates to adenosine A¿3? receptor ligands of the general formula (I), within those preferably antagonists, as well as their salts, solvates and isomers, and the pharmaceutical compositions containing them, to the use of the compounds of the general formula (I), as well as their salts, solvates and isomers, to the preparation of the compounds of the general formula (I) and theirs salts, solvates and isomers, furthermore to the new intermediates of the general formulae (II) and to the preparation thereof.

12 Claims, 1 Drawing Sheet

I

Ia

Figure 1:
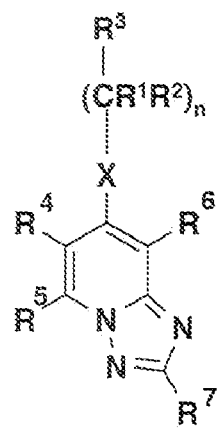

II.

III.

IV.

V.

VI.

VII.

TRIAZOLO-QUINOLIN DERIVATIVES USEFUL AS ADENOSINE RECEPTOR LIGANDS

The application is the National Stage of International Application No. PCT/HU02/00143, filed Dec. 17, 2002.

The present invention relates to adenosine $A_3$ receptor ligands of the general formula (I), within those preferably antagonists, as well as their salts, solvates and isomers, and the pharmaceutical compositions containing them, to the use of the compounds of the general formula (I), as well as their salts, solvates and isomers, to the preparation of the compounds of the general formula (I) and their salts, solvates and isomers, furthermore to the new intermediates of the general formulae (II) and to the preparation thereof.

Adenosine is a well-known component of several endogenous molecules (ATP, $NAD^+$, nucleic acids). Besides, it plays an important regulatory role in many physiological processes. The effect of adenosine on heart function was discovered already in 1929 (Drury and Szentgyörgyi, J Physiol 68:213, 1929). The identification of an increasing number of physiological functions mediated by adenosine and the discovery of new adenosine receptor subtypes give possibilities for therapeutic application of specific ligands (Poulse, S. A. and Quinn, R. J. Bioorganic and Medicinal Chemistry 6:619, 1998).

To date, the receptors for adenosine have been classified into three main classes: $A_1$, $A_2$ and $A_3$. The $A_1$ subtype is partly responsible for inhibiting the adenylate cyclase by coupling to $G_i$ membrane protein, partly influences other second messenger systems. The $A_2$ receptor subtype can be subdivided into two further subtypes—$A_{2a}$ and $A_{2b}$—, which receptors stimulate the adenylate cyclase activity. The sequence of adenosine $A_3$ receptors has been recently identified from rat testis cDNA library. Later it was proved that it corresponds to a novel, functional adenosine receptor. The activation of the $A_3$ receptors is connected also with several second-messenger systems: e.g. inhibiting of adenylate cyclase, and stimulating of phospholipase C and D.

The adenosine receptors are found in several organs and regulate their functions. Both $A_1$ and $A_{2a}$ receptors play important roles in the central nervous system and cardiovascular system. In the CNS, the adenosine inhibits the release of synaptic transmitters which effect is mediated by $A_1$ receptors. In the heart, also the $A_1$ receptors mediate the negative inotropic, chronotropic and dromotropic effects of adenosine. The adenosine $A_{2a}$ receptors located relatively in a higher amount in the striatum, display a functional interaction with dopamine receptors in regulating the synaptic transmission. The $A_{2a}$ adenosine receptors on endothelial and smooth muscle cells are responsible for adenosine-induced vasodilation.

On the basis of mRNA identification, the $A_{2b}$ adenosine receptors are widely distributed in different tissues. They have been identified almost in every cell type, but its expression is the highest in the intestine and the bladder. This subtype probably also has important regulatory function in the regulation of the vascular tone and plays a role in the function of mast cells.

Contrary to $A_1$ and $A_{2a}$ receptors, where the tissue distribution was detected on the protein level, the presence of $A_{2b}$ and $A_3$ receptors was detected on the basis of their mRNA level. Expression levels for $A_3$ adenosine receptors are rather low comparing to other subtypes and highly species dependent. $A_3$ adenosine receptors are expressed primarily in the central nervous system, testis, immune system and appear to be involved in the modulation of mediator release from mast cells in immediate hypersensitivity reaction.

The $A_3$ antagonists published so far in the literature belong to the groups of flavonoides, 1,4-dihydropyridine derivatives, triazoloquinazolines, thiazolonaphthyridines and thiazolopyrimidines. The present invention relates to a novel type of effective $A_3$ antagonists, which have the triazolo-quinolin structure.

For therapeutic use it is essential to ensure that the molecule does not bind, or bind only in the case of very high concentration to the $A_1$, $A_{2a}$ and $A_{2b}$ sub-types of the adenosine receptor. Our present invention relates to the compounds of the general formula (I) as well as their salts, solvates and isomers which have great selectivity for the $A_3$ sub-type of the adenosine receptor.

Our aim was to prepare $A_3$ ligands first of all with triazolo-quinolin structure, and within those preferably antagonists, which have strong antagonistic effect and show high selectivity for the $A_3$ receptor, i.e. they inhibit the $A_3$ receptor in much lower concentration than they inhibit the $A_1$, $A_{2a}$ and $A_{2b}$ receptors. Further aims were to have stability, bioavailability, therapeutic index and toxicity data which make possible to develope the new compounds into drug substances and that due to their favourable enteral absorbtion the compounds can be applied orally.

We have found that the compounds of the general formula (I)—wherein $R^1$ stands for hydrogen atom or a straight or branched $C_{1-4}$ alkyl group;

$R^2$ stands for hydrogen atom or a straight or branched $C_{1-4}$ alkyl group;

$R^3$ stands for hydrogen atom or a straight or branched $C_{1-4}$ alkyl group, or a phenyl group, thienyl group, or furyl group, optionally substituted by one or more straight or branched $C_{1-4}$ alkyl group, straight or branched $C_{1-4}$ alkoxy group, or halogen atom, or for a 5- or 6 membered heteroaromatic ring, containing one, two or three nitrogen atoms, or a 5 membered heteroaromatic ring, containing one nitrogen atom and one oxygen atom or one nitrogen atom and one sulphur atom, optionally substituted by one or more straight or branched $C_{1-4}$ alkyl group, straight or branched $C_{1-4}$ alkoxy group, or halogen atom;

$R^4$ and $R^5$ stand independently from each other for hydrogen atom, or form together an 1,3-butadienyl group, optionally substituted with a methylenedioxy group or one or more straight or branched $C_{1-4}$ alkyl group, straight or branched $C_{1-4}$ alkoxy group, hydroxy group or halogen atom;

$R^6$ stands for hydrogen atom or a cyano group, aminocarbonyl group, $C_{1-4}$ alkoxycarbonyl group, or carboxy group;

$R^7$ stands for hydrogen atom or a straight or branched $C_{1-4}$ alkyl group, or a $C_{1-4}$ alkylene group, optionally substituted by a phenyl group, or for a phenyl group, benzyl group, thienyl group or furyl group, optionally substituted by a methylenedioxy group, or one or more straight or branched $C_{1-4}$ alkyl group, straight or branched $C_{1-4}$ alkoxy group, hydroxy group, trifluoromethyl group, cyano group or halogen atom, amino, mono- or dialkylamino group, or for a 5 or 6 membered heteroaromatic ring, containing one, two or three nitrogen atoms, or a 5 membered heteroaromatic ring, containing one nitrogen atom and one oxygen atom or one nitrogen atom and one sulphur atom, optionally substituted by one or more straight or branched $C_{1-4}$ alkyl group, straight or branched $C_{1-4}$ alkoxy group, or halogen atom;

X stands for a —CH$_2$— group, —NH— group, —NR$^{12}$— group, or a sulphur atom or an oxygen atom or a sulpho group or a sulphoxy group—wherein R$^{12}$ stands for a straight or branched C$_{1-4}$ alkyl group or C$_{3-6}$ cycloalkyl group—;
n stands for zero, 1 or 2— and their salts, solvates, and their optically active isomers and the salts, solvates thereof fulfill the above criteria.

Detailed meanings of the above listed substituents are as follows:

By a straight or branched C$_{1-4}$ alkyl group we mean methyl-, ethyl-, propyl-, isopropyl-, butyl-, isobutyl-, secondary-butyl-, terciary-butyl-, preferably ethyl- or methyl group.

By a straight or branched C$_{1-4}$ alkoxy group we mean methoxy-, ethoxy-, propoxy-, isopropoxy-, butoxy-, isobutoxy-, secondary-butoxy-, terciary-butoxy-, preferably ethoxy- or methoxy group.

The heteroaromatic ring containing one or two or three nitrogen atoms means pyrrol, imidazole, pyrazole, 1,2,3-triazole, 1,2,4-triazole, pyridine, pyrimidine, pyridazine, pyrazine and 1,3,4-triazine ring. The ring is optionally substituted by a C$_{1-4}$ alkyl group.

The heteroaromatic ring containing one nitrogen atom and one oxygen or sulphur atom means oxazole, isoxazole, thiazole, isothiazole ring. The ring is optionally substituted by a C$_{1-4}$ alkyl group.

Salts of the compounds of the general formula (I) mean salts given with inorganic and organic acids and bases. Preferred salts are those given with pharmaceutically accepted acids as for instance hydrochloric acid, sulphuric acid, ethanesulphonic acid, tartaric acid, succinic acid, fumaric acid, malic acid, citric acid.

Solvates mean solvates given with various solvents, as for instance with water or ethanol.

The compounds of the general formula (I) show geometric and optical isomerism, therefore the invention also relates to mixtures of the geometric isomers, to racemic or optically active geometric isomers, as well as to their salts and solvates.

A favourable group of the compounds of the general formula (I) is formed by the compounds of the general formula (Ia), wherein R$^1$ stands for hydrogen atom, or methyl group;
R$^2$ stands for hydrogen atom, or methyl group;
R$^3$ stands for phenyl-, thienyl- or furyl group;
R$^8$, R$^9$, R$^{10}$ and R$^{11}$ independently from each other stand for hydrogen atom, straight or branched C$_{1-4}$ alkyl group, straight or branched C$_{1-4}$ alkoxy group, hydroxy group or halogen atom, or
R$^8$ and R$^{11}$ stand for hydrogen atom and R$^9$ and R$^{10}$ form together a methylenedioxy group,
R$^6$ stands for hydrogen atom, or cyano group;
R$^7$ stands for 4-methoxyphenyl group, 3-methylphenyl group, 3-methoxyphenyl group, 3-thienyl group, 3-pyridyl group, 3-hydroxyphenyl group or 3-furyl group;
X stands for —NH-group or for oxygen atom and
n stands for 1— and their salts, solvates, optically active isomers and the salts, solvates thereof.

Especially favourable are the following compounds complying with the above criteria:
2-(4-Methoxyphenyl)-9-benzylamino-10-cyano-s-triazolo[1,5-α]quinolin,
2-(2-Furyl)-9-(2-furylmethylamino)-10-cyano-s-triazolo[1,5-α]quinolin,
2-(3,4-Methylenedioxyphenyl)-9-(2-furylmethylamino)-10-cyano-s-triazolo[1,5-α]quinolin,
2-(3-Pyridyl)-9-(2-thienylmethylamino)-10-cyano-s-triazolo[1,5-α]quinolin,
2-(3-hydroxyphenyl)-9-(2-thienylmethylamino)-10-cyano-s-triazolo[1,5-α]quinolin, and their salts, solvates, optically active isomers and the salts, solvates thereof.

According to another of its aspects, the present invention also relates to pharmaceutical compositions containing as active principles the compounds of the general formula (I) or their isomers, salts and solvates, which are preferably oral compositions, but inhalable, parenteral and transdermal formulations are also subjects of the invention. The above pharmaceutical compositions may be solids or liquids, such as tablets, pellets, capsules, patches, solutions, suspensions or emulsions. The solid compositions, first of all tablets and capsules are the preferred pharmaceutical forms.

The above pharmaceutical compositions are prepared by applying usual pharmaceutical excipients and by using standard methods.

The compounds of the general formula (I) can be used in treating pathologies, in the development of which A$_3$ receptor plays a role.

The compounds of the present invention having selective activity on the A$_3$ receptor can be used in the therapeutic and/or preventive treatment of disfunctions of the heart, kidney, respiratory system, central nervous system. They inhibit the protective effect of adenosine in growing tumor cells, prevent mast cell degranulation, inhibit the cytokine production, reduce the inraocular pressure, inhibit the TNFα release, inhibit the migration of eosinophils, neutrophils and other immune cells, inhibit the bronchoconstriction and plasma extravasation.

Based on these effects, adenosine A$_3$ receptor antagonists of the present invention may be therapeutically useful as antiinflammatory, antiasthmatic, antiischemic, antidepressant, antiarrhytmic, renal protective, antitumor, antiparkinson and cognitive enhancing drugs. They also may be useful in the treatment or prevention of myocardial reperfusion injury, chronic obstructive pulmonary disease (COPD) and adult respiratory distress syndrome (ARDS) including chronic bronchitis, pulmonary emphysema or dyspnea, allergic reactions (e.g. rhinitis, poison ivy induced responses, urticaria, scleroderma, arthritis) other autoimmune diseases, inflammatory bowel disease, Addison's disease, Crohn's disease, psoriasis, rheumatism, hypertension, neurogical function disorders, glaucoma and diabetes (K. N. Klotz, Naunyn-Schmiedberg's Arch. Pharmacol. 362:382, 2000; P. G. Baraldi és P. A. Borea, TiPS 21:456, 2000).

The compounds of the present invention may be preferable used for the treatment of diseases such as asthma, COPD and ARDS, glaucoma, tumor, allergic and inflammatory diseases, ischemia, hypoxia, arrythmia and renal diseases.

According to another of its aspects, the present invention relates to the use of the compounds of the general formula (I) in the treatment of the above pathologies. Suggested daily dose is 0.1-1000 mg active ingredient depending on the nature and severeness of the disease and on sex, weight etc. of the patient.

Further subject of the invention is the preparation of the compounds of the general formula (I) and of the intermediates of the general formulae (II), (III), and (IV).

The intermediates of the general formula (II) are novel. Substituents of the general formulae (II), (III), and (IV) have the meanings as defined above.

In the process according to our invention an 1,2-diaminoazinium salt of the general formula (II) is reacted with a compound of the general Formula (VII), wherein $R^7$ is defined above and Y stands for hydrogen atom, halogen atom or a $C_{1-4}$ alkoxy group, preferable with the suitable acid halogenide or ester (D. W. Robertson, J. Med. Chem., 28, 717, (1985)) and the compound of the general formula (I) thus obtained is, if desired, transformed into its salts, solvates or, liberated from its salt, solvate and separated into its geometric or optical isomers.

The ring closure can be carried out in the presence of triethylamine in dimethylformamide or of other compounds known as catalysts for ring closures similar type.

The ring closure can be carried out within wide temperature range, preferable within 20° C. and 150° C.

Substituents of the compounds of the general formula (I) may be transformed into each other by known methods.

The compounds of the general formula (II)—wherein the meanings of $R^1$, $R^2$, $R^3$, $R^4$, $R^5$, $R^6$, X and n are as defined above—can be obtained by several known methods, among them the one demonstrated in Scheme 1., by N-amination of the compounds of the formula (III), using N-amination processes known in the organic chemistry (E. E. Glover, R. T. Rowbotton, J. Chem. Soc. Perkin. Trans I., 376, (1976), G. Timári, Gy. Hajós, S. Bátori és A. Messmer, Chem. Ber., 125, 929 (1992)). For N-amination agent preferably O-tosylhydroxylamine can be applied, but other agents known for N-amination can also be used.

The compounds of the general formula (III)—wherein the meanings of $R^1$, $R^2$, $R^3$, $R^4$, $R^5$, $R^6$, X and n are as defined above—can be prepared from the compounds of the formula (IV)—by using methods known per se (Nan Zhang, Bioorg. and Med. Chem. Lett., 10, 2825, (2000)).

The compounds of the general formula (IV)—wherein the meanings of $R^4$, $R^5$, $R^6$ are as defined above—can be prepared from the compounds of the formula (V), by using methods known per se (D. L. Leysen, J. Heterocyclic Chem., 24, 1611, (1987)).

The compounds of the general formula (V)—wherein the meanings of $R^4$, $R^5$, $R^6$ are as defined above—can be prepared by using methods known per se (Pfizer (Inc) U.S. Pat. No. 4,175,193).

The compounds of the invention, of the general formulae (I), (II), (III) and (IV)), their preparation and biological activity are demonstrated in the following Examples, without limiting the scope of claims to the Examples.

Figure 2:
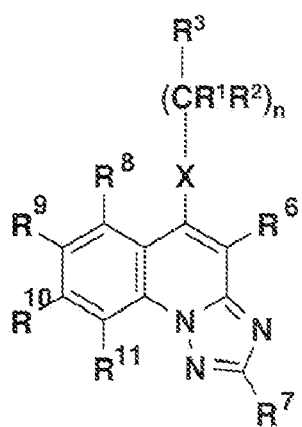
Figure 3:
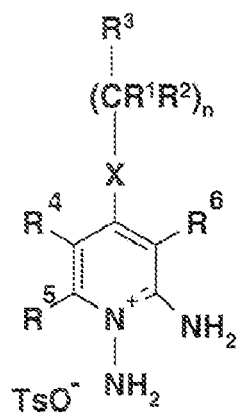
Figure 4:
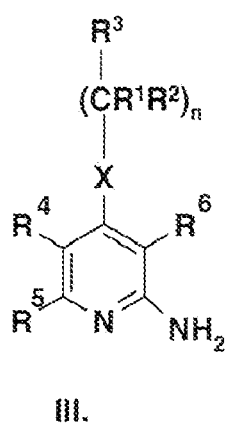
Figure 5:
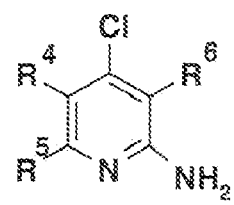
Figure 6:
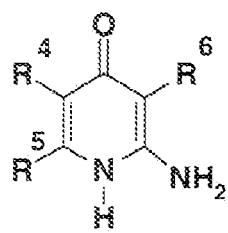
Figure 7:
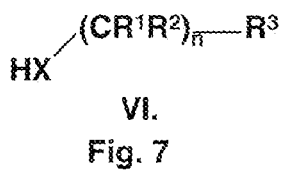
Figure 8:
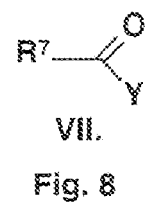

FIG. 1 shows compounds of the formula (I),
FIG. 2 shows compounds of the formula (Ia),
FIG. 3 shows compounds of the formula (II),
FIG. 4 shows compounds of the formula (III),
FIG. 5 shows compounds of the formula (IV),
FIG. 6 shows compounds of the formula (V),
FIG. 7 shows compounds of the formula (VI),
FIG. 8 shows compounds of the formula (VII).

EXAMPLES

Example 1

2-(4-Methoxyphenyl)-9-benzylamino-10-cyano-s-triazolo[1,5-α]quinolin

In general formula (I) $R^1$ and $R^2$ stand for hydrogen atoms, $R^3$ for phenyl group, $R^4$ and $R^5$ form together a 1,3-butadienyl group, $R^6$ stands for cyano group, $R^7$ stands for 4-methoxyphenyl group, the meaning of X is —NH group, n is 1.

a.) 2-Amino-3-cyano-4-chloroquinolin

The mixture of 10 g of 2-amino-3-cyano-4-hydroxyquinolin and 15 ml of phosphoryl chloride is heated under stirring at 110° C. The reaction mixture is cooled down, poured onto 100 ml of ice-water and neutralized with 60 ml of 10% sodium hydroxide solution. The resulting yellow precipitate is filtered off, washed with 50 ml of water. After drying 7.5 g of the title compound is obtained, mp.: 210° C.

NMR, $\delta_H$ (400 MHz, DMSO-$d_6$): 7.21 ppm, (s, 2H, $NH_2$), 7.35-7.40 ppm, (dd, 1H, 6-H), 7.53-7.57 ppm, (d, 1H, 5-H), 7.70-7.75 ppm, (dd, 1H, 7-H), 7.93-7.98 ppm, (d, 1H, 8-H)

b.) 2-Amino-3-cyano-4-benzylaminoquinolin 5 g of 2-amino-3-cyano-4-chloroquinolin and 11 ml of benzylamine are heated under stirring at 130° C. The reaction mixture is poured onto 50 ml of water, the resulting precipitate is filtered off, washed with 50 ml of water. The pale-yellow precipitate is recrystallized from dimethylformamide to obtain 5.2 g of the title compound. Mp.: 206° C.

NMR, $\delta_H$ (400 MHz, DMSO-$d_6$): 5.02-5.03 ppm, (d, 2H, N—$CH_2$), 6.22 ppm, (s, 2H, $NH_2$), 7.14-7.16 ppm, (dd, 1H, 6-H), 7.24-7.26 ppm, (dd, 1H, 5-H), 7.30 ppm, (s, 5H, Ph), 7.50-7.52 ppm, (dd, 1H, 7-H), 8.16-8.19 ppm, (d, 1H, 8-H), 8.30-8.33 ppm, (t, 1H, NH)

c.) 1,2-Diamino-3-cyano-4-benzylamino-quinolinium-tozylate

To the solution of 2.0 g of 2-amino-3-cyano-4-benzylaminoquinolin in 30 ml of dimethylformamide 1.78 g O-tosylhydroxylamine in 20 ml dichloromethane are dropped at 20° C. within 15 minutes. The reaction mixture is stirred for 5 hour, than the precipitate is filtered off. The resulting white crystalline material is recrystallized from acetonitrile to give 3.1 g of the title compound, mp.: 207° C.

d. 2-(4-Methoxyphenyl)-9-benzylamino-10-cyano-s-triazolo[1,5-α]quinolin

To the mixture of 2.0 g. 1,2-diamino-3-cyano-4-benzylamino-quinolinium-tozylate and 15 ml pyridine 2 g of anise acid chloride are added. The reaction mixture is stirred for 8 hour at 100° C. The mixture is poured onto 50 ml of water, the crystals precipitated are filtered off and recrystallised from acetonitrile to give 1.1 g of the title compound. Mp.: 237C.

NMR, $\delta_H$ (400 MHz, DMSO-$d_6$): 8.78 ppm (t,1H), 8.58 (d,1H), 8.38 (d,1H), 8.10 (d,2H), 7.98 (t,1H), 7.39 (m, 5H), 7.07 (d,2H), 5.14 (d,2H), 3.82 (s,3H).

Example 2

2-(2-Furyl)-9-(2-furylmethylamino)-10-cyano-s-triazolo[1,5-α]quinolin

In the general formula (I) the meaning of $R^1$ and $R^2$ is hydrogen atom, $R^3$ is 2-furyl group, $R^4$ and $R^5$ form together an 1,3-butadienyl group, $R^6$ stands for cyano group, $R^7$ stands for 2-furyl group, X means —NH-group, n is 1.

a.) 2-Amino-3-cyano-4-(2-Furylmethylamino)-quinolin 5 g of 2-amino-3-cyano-4-chloroquinolin and 1 ml of furylmethylamine (furfurylamine) are heated under stirring at 130° C. The reaction mixture is poured onto 50 ml of water, the resulting precipitate is filtered off, washed with 50 ml of water. The pale-yellow precipitate is recrystallized from 20 ml ethanol to obtain 4.8 g of the title compound. Mp.: 208° C.

b.) 1,2-Diamino-3-cyano-4-(2-furylmethylamino)-quinolinium-tozylate

To the solution of 2.0 g of 2-amino-3-cyano-4-(2-furyl-methylamino)-quinolin in 30 ml dimethylformamide 1.78 g O-tozyl-hydroxylamine in 20 ml dichloromethane are dropped at 20° C. within 15 minutes. The reaction mixture is stirred for 5 hour, than the precipitated white cristalline material is filtered off and recrystallized from acetonitrile to give 2.1 g of the title compound, mp.: 211° C.

c.). 2-(2-Furyl)-9-(2-furylmethylamino)-10-cyano-s-triazolo[1,5-α]quinolin

To the mixture of 2.0 g. 1,2-diamino-3-cyano-4-(2-furyl-methylamino)-quinolinium-tozylate and 15 ml pyridine 2 g of furan-2-carboxylic-acid-chloride are added. The reaction mixture is stirred for 8 hour at 100° C. The mixture is poured onto 50 ml of water, the crystals precipitated are filtered off and recrystallised from acetonitrile to give 1.1 g of the title compound. Mp.: 203C.
NMR, $δ_H$ (400 MHz, DMSO-$d_6$): 8.74 ppm (t,1H), 8.52 (d,1H), 8.32 (d,1H), 7.90 (m,3H), 7.63 (m,2H), 7.14 (m,1H), 6.68 (m,1H), 6.44 (m,2H), 5.11 (d,2H).

Example 3

2-(3,4-Methylendioxyphenyl)-9-(2-furylmethy-lamino)-10-ciano-s-triazolo[1,5-α]quinolin In the general formula (I) the meaning of $R^1$ and $R^2$ is hydrogen atom, $R^3$ is furyl group, $R^4$ and $R^5$ form together an 1,3-butadienyl group, $R^6$ stands for cyano group, $R^7$ stands for 3,4 methylendioxyphenyl group, X means —NH-group, n is 1.

a.). 2-(3,4-Methylendioxyphenyl)-9-(2-furylmethy-lamino)-10-cyano-s-triazolo[1,5-α]quinolin To the mixture of 2.0 g. 1,2-diamino-3-cyano-4-(2-furyl-methylamino)-quinolinium-tozylate and 15 ml pyridine 2 g of 3,4-methylendioxy-benzoic-acid-chloride are added. The reaction mixture is stirred for 8 hour at 100° C. The mixture is poured onto 50 ml of water, the crystals precipitated are filtered off and recrystallised from acetonitrile to give 1.4 g of the title compound. Mp.: 185C.

NMR, $δ_H$ (400 MHz, DMSO-$d_6$): 8.55 ppm (m,1H), 8.51 (d,1H), 8.31 (d,1H), 7.93 (t,1H), 7.57-7.70 (m,3H), 7.05 (d,1H), 6.44 (m,2H), 6.11 (s,2H), 5.08 (d,2H).

Example 4

2-(3-Pyridyl)-9-(2-tienylmethylamino)-10-cyano-s-triazolo[1,5-α]quinolin

In the general formula (I) the meaning of $R^1$ and $R^2$ is hydrogen atom, $R^3$ is 2-tienyl group, $R^4$ and $R^5$ form together an 1,3-butadienyl group, $R^6$ stands for cyano group, $R^7$ stands for 3-pyridyl group, X means —NH-group, n is 1.

a.)2-amino-3-cyano-4-(2-tienylmethylamino)-quinolin 5 g of 2-amino-3-cyano-4-chloroquinolin and 11 ml of tienylmethylamine are heated under stirring at 130° C. The reaction mixture is poured onto 50 ml of water, the resulting precipitate is filtered off, washed with 50 ml of water. The pale-yellow precipitate is recrystallized from 25 ml ethanol to obtain 5.2 g of the title compound. Mp.: 208° C.

b.) 1,2-Diamino-3-cyano-4-(2-tienylmethylamino)-quinolinium-tozylate

To the solution of 2.0 g of 2-amino-3-cyano-4-(2-tienyl-methylamino)-quinolin in 30 ml dimethylformamide 1.78 g O-tozyl-hydroxylamine in 20 ml dichloromethane are dropped at 20° C. within 15 minutes. The reaction mixture is stirred for 5 hour, than the precipitated white cristalline material is filtered off and recrystallized from acetonitrile to give 2.1 g of the title compound, mp.: 198° C.

c.). 2-(3-Pyridyl)-9-(2-tienylmethylamino)-10-cyano-s-triazolo[1,5-α]quinolin

To the mixture of 2.0 g. 1,2-diamino-3-cyano-4-(2-tienyl-methylamino)-quinolinium-tozylate and 20 ml dimethylfor-mamide 4 ml of triethylamine and 4 g of pyridine-3-carboxaldehyde are added. The reaction mixture is stirred for 8 hour at 100° C. The mixture is poured onto 50 ml of water, the crystals precipitated are filtered and recrystallised from acetonitrile to give 0.8 g of the title compound. Mp.: 249C.
NMR, $δ_H$ (400 MHz, DMSO-$d_6$): 9.25 ppm (s,1H), 8.71 (m,2H), 8.35 (m,3H), 7.86 (m,1H), 7.51 (m,3H), 7.17 (m,1H), 6.98 (m,1H), 5.25 (d,2H).

Example 5

2-(3-Hydroxyphenyl)-9-(2-tienylmethylamino)-10-cyano-s-triazolo[1,5-α]quinolin In the general formula (I) the meaning of $R^1$ and $R^2$ is hydrogen atom, $R^3$ is 2-tienyl group, $R^4$ and $R^5$ form together an 1,3-butadienyl group, $R^6$ stands for cyano group, $R^7$ stands for 3-hydroxyphenyl group, X means —NH-group, n is 1.

a.). 2-(3-Hydroxyphenyl)-9-(2-tienylmethylamino)-10-cyano-s-triazolo[1,5-α]quinolin To the mixture of 2.0 g. 1,2-diamino-3-cyano-4-(2-tienyl-methylamino)-quinolinium-tozylate and 20 ml dimethylfor-mamide 4 ml of triethylamine and 4 g of 3-hydroxy-benzaldehyde are added. The reaction mixture is stirred for 8 hour at 100° C. The mixture is poured onto 50 ml of water, the crystals precipitated are filtered off and recrystallised from acetonitrile to give 0.9 g of the title compound. Mp.: 248C.

NMR, $\delta_H$ (400 MHz, DMSO-$d_6$): 9.66 ppm (s,1H), 8.81 (m,1H), 8.52 (m,1H), 8.35 (m,1H), 796 (m,1H), 7.62 (m,3H), 7.44 (m,1H), 7.32 (m,1H), 7.18 (m,1H), 7.01 (m,1H), 6.88 (m,1H), 5.29 (d,2H);

Structure and physical characteristics of further compounds of general formula (I) prepared by the method described in Example 1. are shown in Table I.

TABLE I (I)

| No.: | X | R³ | R⁴ | R⁵ | R⁷ | Mp: [° C.] |
|---|---|---|---|---|---|---|
| 6. | NH | phenyl | H | H | phenyl | 271 |
| 7. | NH | phenyl | H | H | pyridin-3-yl | 259 |
| 8. | NH | phenyl | H | H | pyridin-4-yl | 246 |
| 9. | NH | phenyl | H | H | 4-methylphenyl | 266 |
| 10. | NH | phenyl | H | H | 2-hydroxyphenyl | 209 |
| 11. | NH | phenyl | H | H | 3-hydroxyphenyl | 260 |
| 12. | NH | phenyl | H | H | styryl | 214 |
| 13. | NH | phenyl | H | H | 3-methoxyphenyl | 264 |

TABLE I-continued (I)

| No.: | X | R³ | R⁴ | R⁵ | R⁷ | Mp: [° C.] |
|---|---|---|---|---|---|---|
| 14. | NH | phenyl | H | H | 2-chlorophenyl | 245 |
| 15. | NH | phenyl | H | H | 4-chlorophenyl | 285 |
| 16. | NH | phenyl | H | H | 2-furyl | 274 |
| 17. | NH | phenyl | H | H | 2-pyridyl | 295 |
| 18. | NH | phenyl | H | H | 2-thienyl | 280 |
| 19. | NH | phenyl | H | H | 4-hydroxyphenyl | 273 |
| 20. | NH | phenyl | H | H | 4-methoxyphenyl | 253 |
| 21. | NH | phenyl | H | H | 3-hydroxy-4-methoxyphenyl | 280 |

TABLE I-continued
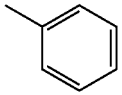
(I)
| No.: | X | R³ | R⁴ | R⁵ | R⁷ | Mp: [° C.] |
|---|---|---|---|---|---|---|
| 22. | NH | 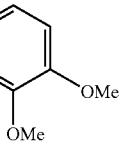 | H | H | 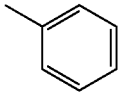 | 230 |
| 23. | NH | 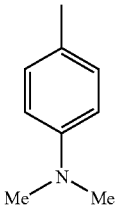 | H | H | 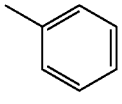 | 243 |
| 24. | NH | 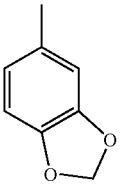 | H | H | 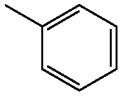 | 286 |
| 25. | NH |  | H | H | —Me | 218 |
| 26. | NH | 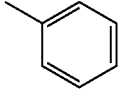 | H | H |  | 198 |
| 27. | NH | 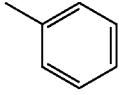 | H | H | 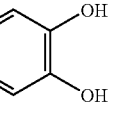 | 317 |
| 28. | NH | 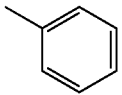 |  | |  | 160 |
| 29. | NH | 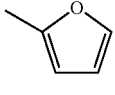 |  | | 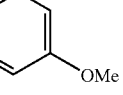 | 231 |

TABLE I-continued (I)

| No.: | X | R³ | R⁴ | R⁵ | R⁷ | Mp: [° C.] |
|---|---|---|---|---|---|---|
| 30. | NH | 2-furyl | | | 3-MeO-phenyl | 179 |
| 31. | NH | 2-furyl | | | 4-HO-phenyl | 250 |
| 32. | NH | 2-thienyl | | | 4-MeO-phenyl | 219 |
| 33. | NH | 2-thienyl | | | 2-thienyl | 220 |
| 34. | NH | 2-thienyl | | | 4-pyridyl | 250 |
| 35. | NH | phenyl | | | 3-F-phenyl | 158 |
| 36. | NH | phenyl | | | 4-CF₃-phenyl | 195 |

TABLE I-continued (I)

| No.: | X | R³ | R⁴ | R⁵ | R⁷ | Mp: [° C.] |
|---|---|---|---|---|---|---|
| 37. | NH | 2-thienyl | | | benzo[1,3]dioxol-5-yl (Me-substituted) | 298 |
| 38. | NH | 2-thienyl | | | 3-fluorophenyl (Me-substituted) | 239 |
| 39. | NH | 2-thienyl | | | 3-(trifluoromethyl)phenyl (Me-substituted) | 216 |
| 40. | NH | 2-thienyl | | | 3-methylphenyl (Me-substituted) | 217 |
| 41. | NH | phenyl | | | 4-iodophenyl (Me-substituted) | 260 |
| 42. | NH | phenyl | MeO | | 4-methoxyphenyl | 254 |
| 43. | O | phenyl | | | 4-methoxyphenyl (Me-substituted) | 232 |
| 44. | S | phenyl | | | benzo[1,3]dioxol-5-yl (Me-substituted) | 207 |
| 45. | S=O | phenyl | | | benzo[1,3]dioxol-5-yl (Me-substituted) | 248 |

TABLE I-continued
(I)
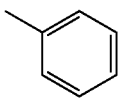
| No.: | X | R³ | R⁴ | R⁵ | R⁷ | Mp: [° C.] |
|---|---|---|---|---|---|---|
| 46. | SO₂ |  | 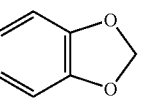 | | 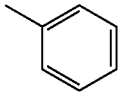 | 301 |
| 47. | S |  | 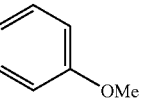 | | 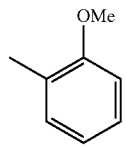 | 160 |
Structure and physical characteristics of the intermediates of the general formula (III) prepared by the method described in Example 1. are shown in Table (II)
TABLE II
(III)
| No.: | R¹ | R² | R³ | R⁴ | R⁵ | X | n | Mp: [° C.] |
|---|---|---|---|---|---|---|---|---|
| 48 | H | H | 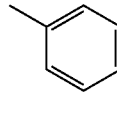 | |  | NH | 1 | 192 |
| 49 | H | H | 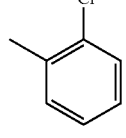 | |  | NH | 1 | 202 |
| 49 | H | H | 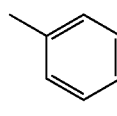 | |  | NH | 1 | 250 |
| 50. | H | H |  | |  | NH | 1 | 167 |

TABLE II-continued (III)

$$\text{structure with } R^4, R^5, X\text{-}(CR^1R^2)_n\text{-}R^3, CN, NH_2 \text{ on pyridine}$$

| No.: | R¹ | R² | R³ | R⁴ | R⁵ | X | n | Mp: [° C.] |
|---|---|---|---|---|---|---|---|---|
| 51. | H | ⫶Me (α) | phenyl | | 1-propenyl | NH | 1 | 183 |
| 52. | H | ▲Me (β) | phenyl | | 1-propenyl | NH | 1 | 182 |
| 53. | H | H | phenyl | | 1-propenyl | NH | 2 | 172 |
| 54. | H | H | 3,4-dimethoxyphenyl | | 1-propenyl | NH | 2 | 143 |
| 55. | H | ⫶Me (α) | phenyl | | 1-propenyl | NH | 2 | 129 |
| 56. | H | ▲Me (β) | phenyl | | 1-propenyl | NH | 2 | 136 |
| 57 | H | H | phenyl | | 1-propenyl | N—Me | 1 | 212 |
| 58 | H | H | phenyl | | 1-propenyl | S | 1 | 168 |
| 59 | H | H | phenyl | | 1-propenyl | O | 1 | 213 |
| 60 | H | H | phenyl | Cl | vinyl | NH | 1 | 234 |
| 61 | H | H | 2-furyl | Cl | vinyl | NH | 1 | 221 |

TABLE II-continued (III)

No.: R¹  R²  R³           R⁴  R⁵        X   n   Mp: [° C.]
62.  H   H   (phenyl)     Me  (isopropenyl)  NH  1   198
63.  H   H   (phenyl)     MeO (1-methoxyvinyl) NH  1   201
64.          (phenyl)         (vinyl-CH=CH₂)   NH  0   214

Structure and physical characteristics of the intermediates of the general formula (IV) prepared by the method described in Example 1. are shown in Table (III)

TABLE III

| No: | R⁴ + R⁵ | Mp [° C.] |
|---|---|---|
| 65. | HO-C(=CH₂)-CH=CH₂ | 360 |
| 66. | Cl-C(=CH₂)-CH=CH₂ | 250 |
| 67. | CH₂=CH-C(Cl)=CH₂ | 278 |
| 68. | Me-C(=CH₂)-CH=CH₂ | 283 |
| 69. | MeO-C(=CH₂)-CH=CH₂ | 360 |

TABLE III-continued

| No: | R⁴ + R⁵ | Mp [° C.] |
|---|---|---|
| 70. | CH₂=CH-CH=CH-OMe | 234 |
| 71. | Me-CH=CH-CH=CH₂ | 246 |
| 72. | CH₂=CH-CH=CH-Me | 267 |
| 73. | I-C(=CH₂)-CH=CH₂ | 293 |

Example 74

Tablets of the following composition are made by known methods used in the pharmaceutical industry

| Active ingredient | 25 mg |
|---|---|
| Lactose | 50 mg |
| Avicel | 21 mg |
| Crospovidone | 3 mg |
| Magnesium stearate | 1 mg |

Biology

Methods

Human Adenosine $A_3$ Receptor Binding

Preparing membrane suspension: collect CHO cells expressing hA3 receptors by washing three times with ice cold PBS; centrifugate at 1000×g 10 min, homegenize for 15 sec in buffer (50 mM Tris, 10 mM $MgCl_2$, 1 mM EDTA, pH 8.0), centrifugate at 43.000×g for 10 min (Sigma 3K30), suspense the membrane preparation in the buffer mentioned above, store the aliquots at −80 C.

Binding protocol: incubate CHO-$hA_3$ membrane preparation (2 µg protein content) in incubation buffer (50 mM Tris, 10 mM $MgCl_2$, 1 mM EDTA, 3 U/mL adenosine deaminase, pH 8.0), in the presence of 0.5 nM [$^{125}$I]AB-MECA (p-amino-benzyl-methylcarboxamido-adenosine) (100.000 cpm) and 100 µM R-PIA ($N^6$-[L-2-phenylisopropyl]adenosine) to define non-specific binding or test compound in a total volume of 50 µL for 1 hr at room temperature. Filter over Whatman GF/B glass fibre filters (presoaked in 0.5% polyethylenimine for 3 hours), wash 4× with 1 mL ice-cold 50 mM Tris, 10 mM $MgCl_2$, 1 mM EDTA (pH 8.0) on 96-well Brandel Cell Harvester. Detection of activity: in gamma-counter (1470 Wizard, Wallac). Inhibition [%]=100−((activity in the presence of test compound−non-specific activity)/(total activity−non-specific activity))*100

Human Adenosine $A_1$ Receptor Binding

Preparing membrane suspension: collect CHO cells expressing $hA_1$ receptors by washing three times with ice cold PBS, centrifugate at 1000×g 10 min, homogenize for 15 sec in buffer (50 mM Tris, pH 7.4), centrifugate at 43.000×g for 10 min (Sigma 3K30), suspense the membrane preparation in the buffer mentioned above, store the aliquots at −80 C.

Binding protocol: incubate CHO-$hA_1$ membrane preparation (50 µg protein content) in incubation buffer (50 mM Tris, 3 U/mL adenosine deaminase, pH 7.4), 10 nM [$^3$H] CCPA (2-chloro-$N^6$-cyclopenthyl-adenosine) (80.000 dpm) and 10 µM R-PIA $N^6$-[L-2-phenylisopropyl]adenosine) to define the non-specific binding or test compound in a total volume of 100 µL for 3 hr at room temperature. Filter over Whatmnan GF/B glass fibre filters (presoaked in 0.5% polyethylenimine for 3 hours), wash 4× with 1 mL ice-cold 50 mM Tris (pH 7.4) on 96-well Brandel Cell Harvester. Detection of activity: in 96-well plate in the presence of HiSafe-3 cocktail in beta-counter (1450 Microbeta, Wallac). Inhibition [%]=100−((activity in the presence of test compound−non-specific activity)/(total activity−non-specific activity))*100

Human Adenosine $A_{2a}$ Receptor Binding

Binding protocol: incubate 7 µg of membranes (human $A_{2a}$ adenosine receptors transfected into HEK-293 cells, source: Receptor Biology, Inc.), buffer (50 mM Tris-HCl, 10 mM $MgCl_2$, 1 mM EDTA, 2 U/mL adenosine deaminase, pH 7.4), 20 nM [$^3$H]CGS-21680 (2-[p-(2-carbonylethyl)phenyl-ethylamino]-5'-N-ethylcarboxamido-adenosine) (200.000 dpm) and 50 µM NECA (5'-N-ethylcarboxamido-adenosine) to define the non-specific binding or test compound in a total volume of 100 µl for 90 min at room temperature. Filter over Whatman GF/B glass fibre filters (presoaked in 0.5% polyethylenimine), wash 4× with 1 mL ice-cold 50 mM Tris, 10 mM $MgCl_2$, 1 mM EDTA, 0.9% NaCl, pH 7.4) on 96-well Brandel Cell Harvester. Detection of activity: in 96-well plate in the presence of HiSafe-3 cocktail in beta-counter (1450 Microbeta, Wallac). Inhibition [%]=100−((activity in the presence of test compound−non-specific activity)/(total activity−non-specific activity))*100

Human Adenosine $A_{2b}$ Receptor Binding

Binding protocol: incubate 20.8 µg of membranes (human $A_{2b}$ adenosine receptors transfected into HEK-293 cells, source: Receptor Biology, Inc.), buffer (50 mM Tris-HCl, 10 mM $MgCl_2$, 1 mM EDTA, 0.1 mM benzamidine, 2 U/mL adenosine deaminase, pH 6.5), 32.4 nM [$^3$H]DPCPX (8-cyclopenthyl-1,3-dipropylxanthine) (800.000 dpm) and 100 µM NECA (5'-N-ethylcarboxamido-adenosine) to define non-specific binding or test compound in a total volume of 100 µL for 30 min at room temperature. Filter over Whatman GF/C glass fibre filters (presoaked in 0.5% polyethylenimine), wash 4× with 1 mL ice-50 mM Tris-HCl (pH 6.5) on 96-well Brandel Cell Harvester. Detection of activity: in 96-well plate in the presence of HiSafe-3 cocktail in beta-counter (1450 Microbeta, Wallac). Inhibition [%]=100−((activity in the presence of test compound−non-specific activity)/(total activity−non-specific activity))*100

Results

We consider the compounds as biologically active ones if they inhibit the binding of the radioligand on human adenosine $A_3$ receptors with an activity above 80% at 1 µM in our experimental conditions.

The dissociation constant ($K_d$) of [$^{125}$I]AB-MECA on CHO-$hA_3$ membrane preparation is determined by isotope saturation-studies with the help of Scatchard analysis. (G. Scatchard, Ann. N. Y. Acad. Sci. 51:660, 1949). The $IC_{50}$ is converted to an affinity constant ($K_i$) by application of the Cheng-Prusoff equation (Y. J. Cheng and W. H. Prusoff, Biochem. Pharmacol. 22:3099, 1973).

Several compounds of the general formula (I), (II), (III) and (IV) display remarkable biological effects. The compounds or the general formula (Ia), defined in claim 2, as a subgroup of the general formula (I), defined in claim 1, exert the most important activities. Except of 9 compounds, their $K_i$ values are not higher than 20 nM. The compounds given as examples are especially advantageous. Their $K_i$ values in human adenosine $A_3$ receptor binding studies are between 3.5 and 0.78 nM. The $K_i$ values or the most advantageous compounds are 0.82 and 0.78 nM.

The compounds possess proper bioviabilities and exert at least 1,000-fold selectivity in respect of human adenosine $A_1$, $A_{2a}$ and $A_{2b}$ receptor subtypes.

Further, the duration of their action at intravenous and oral administration is long enough, their $ED_{50}$ values are low, their toxicological and side-effect profiles are advantageous.

Data above make the compounds of the general formula (I) probable for therapeutic applications.

The invention claimed is:

1. A compound of formula (I)

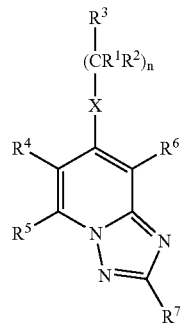

(I)

wherein $R^1$ is hydrogen atom or a straight or branched $C_{1-4}$ alkyl group;

$R^2$ is hydrogen atom or a straight or branched $C_{1-4}$ alkyl group;

$R^3$ is a phenyl group, thienyl group, or furyl group, wherein the phenyl group, thienyl group, or furyl group is optionally substituted by one or more straight or branched $C_{1-4}$ alkyl group, straight or branched $C_{1-4}$ alkoxy group, or halogen atom, or a 5 or 6 membered heteroaromatic ring, containing one, two or three nitrogen atoms, or a 5 membered heteroaromatic ring, containing one nitrogen atom and one oxygen atom or one nitrogen atom and one sulphur atom, wherein the 5 or 6 membered heteroaromatic ring is optionally substituted by one or more straight or branched ($C_{1-4}$ alkyl group, straight or branched $C_{1-4}$ alkoxy group, or halogen atom;

$R^4$ and $R^5$ are independently from each other for hydrogen atom, or form together an 1,3-butadienyl group, optionally substituted with a methylendioxy group or one or more straight or branched $C_{1-4}$ aklyl group, straight or branched $C_{1-4}$ alkoxy group, hydroxy group or halogen atom;

$R^6$ is hydrogen atom, a cyano group, aminocarbonyl group, $C_{1-4}$ alkoxycarbonyl group, or carboxy group;

$R^7$ is hydrogen atom, a straight or branched $C_{1-4}$ alkyl group, a $C_{1-4}$ alkylene group, optionally substituted by a phenyl group, a phenyl group, benzyl group, thienyl group or furyl group, wherein the phenyl group, benzyl group, thienyl group, or furyl group is optionally substituted by a methylendioxy group, or one or more straight or branched $C_{1-4}$ alkyl group, straight or branched $C_{1-4}$ alkoxy group, hydroxy group, trifluoromethyl group, cyano group, halogen atom, amino, or mono- or dialkylamino group, or a 5 or 6 membered heteroaromatic ring, containing one, two or three nitrogen atoms, or a 5 membered heteroaromatic ring, containing one nitrogen atom and one oxygen atom or one nitrogen atom and one sulphur atom, wherein the 5 or 6 membered heteroaromatic ring is optionally substituted by one or more straight or branched $C_{1-4}$ alkyl group, straight or branched $C_{1-4}$ alkoxy group, or halogen atom;

X is a —$CH_2$— group, —NH— group, —$NR^{12}$— group, a sulphur atom, an oxygen atom, a sulpho group or a sulphoxy group wherein $R^{12}$ is a straight or branched $C_{1-4}$ alkyl group or $C_{3-6}$ cycloalkyl group; and n stands for 0, 1 or 2;

provided that when $R^4$ and $R^5$ are both hydrogen atom, $R^6$ is hydrogen atom or a cyano group, $R^7$ is hydrogen atom, a straight or branched $C_{1-4}$ alkyl group, or a phenyl group, and X is a —$CH_2$— group, then $R^3$ $(CR^1R^2)_n$- taken together is other than hydrogen atom straight or branched $C_{1-4}$ alkyl group;

or its salt, solvate or optically active isomer thereof, or a salt or solvate of the optically active isomer.

2. The compound of formula (Ia) according to claim 1,

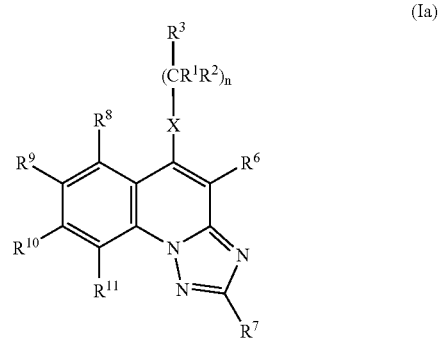

(Ia)

wherein $R^1$ is hydrogen atom or a straight or branched $C_{1-4}$ alkyl group;

$R^2$ is hydrogen atom or a straight or branched $C_{1-4}$ alkyl group;

$R^3$ is a phenyl group, thienyl group, or furyl group, wherein the phenyl group, thienyl group, or furyl group is optionally substituted by one or more straight or branched $C_{1-4}$ alkyl group, straight or branched $C_{1-4}$ alkoxy group, or halogen atom, or a 5 or 6 membered heteroaromatic ring, containing one, two or three nitrogen atoms, or a 5 membered heteroaromatic ring, containing one nitrogen atom and one oxygen atom or one nitrogen atom and one sulphur atom, wherein the 5 or 6 membered heteroaromatic ring is optionally substituted by one or more straight or branched $C_{1-4}$ alkyl group, straight or branched $C_{1-4}$ alkoxy group, or halogen atom;

$R^8$, $R^9$, $R^{10}$ and $R^{11}$ independently from each other are hydrogen atom, straight or branched $C_{1-4}$ alkyl group, straight or branched $C_{1-4}$ alkoxy group, hydroxy group or halogen atom, or $R^8$ and $R^{11}$ are hydrogen atom and $R^9$ and $R^{10}$ form together a methylendioxy group, $R^6$ is hydrogen atom, a cyano group, aminocarbonyl group, $C_{1-4}$ alkoxycarbonyl group, or carboxy group;

$R^7$ is hydrogen atom, a straight or branched $C_{1-4}$ alkyl group, a $C_{1-4}$ alkylenen group, optionally substituted by a phenyl group, a phenyl group, benzyl group, thienyl group or furyl group, wherein the phenyl group, benzyl group, thienyl group, or furyl group is optionally substituted by a methylendioxy group, or one or more straight or branched C$_{1-4}$ alkyl group, straight or branched C$_{1-4}$ alkoxy group, hydroxy group, trifluoromethyl group, cyano group, halogen atom, amino, or mono- or dialkylamino group, or a 5 or 6 membered heteroaromatic ring, containing one, two or three nitrogen atoms, or a 5 membered heteroaromatic ring containing one nitrogen atom and one oxygen atom or one nitrogen atom and one sulphur atom, wherein the 5 or 6 membered heteroaromatic ring is optionally substituted by one or more straight or branched C$_{1-4}$ alkyl group, straight or branched C$_{1-4}$ alkoxy group, or halogen atom;

X is a —CH$_2$— group, —NH— group, —NR$^{12}$— group, a sulphur atom, an oxygen atom, a sulpho group or a sulphoxy group wherein R$^{12}$ stands for a straight or branched C$_{1-4}$ alkyl group or C$_{3-6}$ cycloalkyl group; and n stands for 0, 1 or 2;

or its salt, solvate, or optically active isomer thereof, or a salt or solvate of the optically active isomer.

3. The compound of formula (Ia) according to claim 2, wherein

R$^1$ is hydrogen atom, or methyl group;

R$^2$ is hydrogen atom, or methyl group;

R$^3$ is phenyl or thienyl or furyl group;

R$^8$, R$^9$, R$^{10}$ and R$^{11}$ independently from each other are hydrogen atom, straight or branched C$_{1-4}$ alkyl group, straight or branched C$_{1-4}$ alkoxy group, hydroxy group or halogen atom, or R$^8$ and R$^{11}$ are hydrogen atom and R$^9$ and R$^{10}$ form together a methylendioxy group;

R$^6$ is hydrogen atom, or cyano group;

R$^7$ is 4-methoxyphenyl group, 3-methylphenyl group, 3-methoxyphenyl group, 3-thienyl group, 3-pyridyl group, 3-hydroxyphenyl group or 3-furyl group;

X is —NH— group or oxygen atom; and n is 1;

or its salt, solvate, or optically active isomer thereof, or a salt or solvate of the optically active isomer.

4. The compound according to claim 2 as follows:

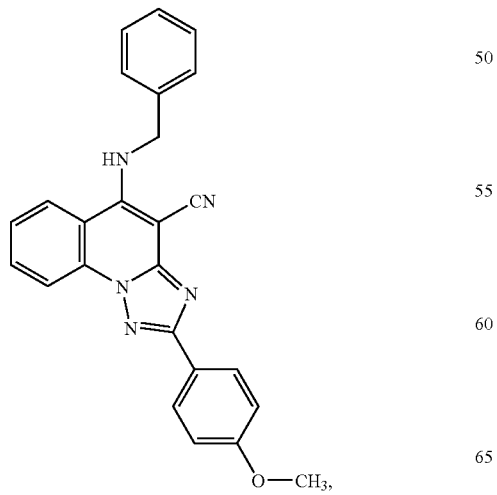

-continued

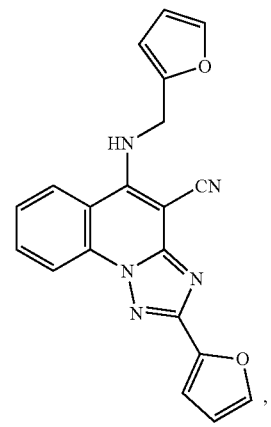

,

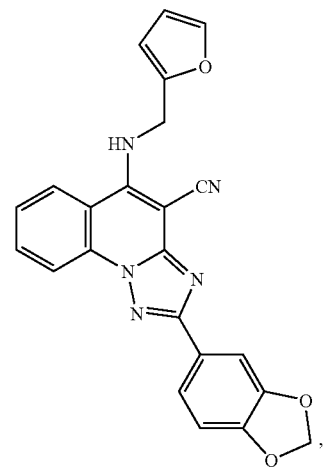

,

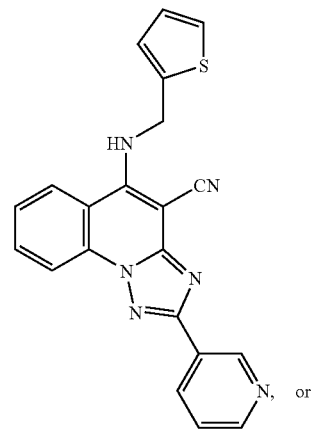

, or

-continued

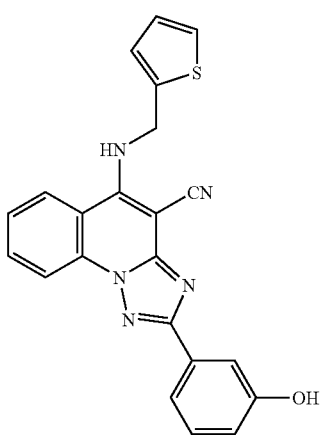

or its salt, solvate, or optically active isomer thereof, or a salt or solvate of the optically active isomer.

5. A process for the preparation of a compound of formula (I),

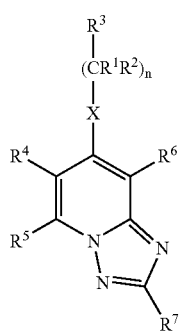
(I)

its salt, solvate, or optically active isomer thereof, or a salt or solvate of the optically active isomer—wherein in the formula $R^1, R^2, R^3, R^4, R^5, R^6, R^7, R^8, X$ and n have the same meaning as defined in claim 1, comprising reacting a 1,2-diamino-pyridinium salt of formula (II),

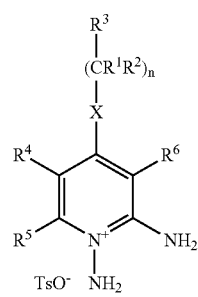
(II)

wherein $R^1, R^2, R^3, R^4, R^5, R^6, R^7, X$ and n have the same meaning as defined in claim 1, with a compound of Formula (VII)

(VII)

wherein $R^7$ is as defined in claim 1 to form the compound of formula (I) corresponding thereto.

6. The process according to claim 5 wherein the reaction is carried out in dimethylformamide in the presence of triethylamine where for the compound of the formula (VII) Y is hydrogen atom.

7. The process according to claims 5 where for the compound of the formula (VII) Y is halogen atom.

8. A pharmaceutical composition comprising a pharmaceutically effective amount of the compound according to claim 1, or its salt, solvate, or optically active isomer thereof, or a salt or solvate of the optically active isomer in admixture with one or more excipients.

9. A pharmaceutical composition comprising a pharmaceutically effective amount of the compound according to claim 2, or its salt, solvate, or optically active isomer thereof, or a salt or solvate of the optically active isomer in admixture with one or more excipients.

10. A pharmaceutical composition comprising a pharmaceutically effective amount of the compound according to claim 4, or its salt, solvate, or optically active isomer thereof, or a salt or solvate or the optically active isomer in admixture with one or more excipients.

11. A compound of formula (II)

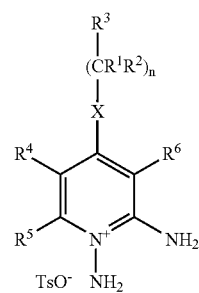
(II)

wherein $R^1, R^2, R^3, R^4, R^5, R^6, X$ and n have the same meaning as defined in claim 1.

12. A pharmaceutical composition comprising a pharmaceutically effective amount of the compounds according to claim 3, or its salt, solvate, or optically active isomer thereof, or a salt or solvate of the optically active isomer in admixture with one or more excipients.

* * * * *